(12) United States Patent
Spencer et al.

(10) Patent No.: US 7,718,106 B2
(45) Date of Patent: May 18, 2010

(54) MEDICAL DEVICES AND RELATED SYSTEMS AND METHODS

(75) Inventors: Steven M. Spencer, Minneapolis, MN (US); Robert Warner, Woodbury, MN (US); Michael S. Arney, Minneapolis, MN (US); John Blix, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 431 days.

(21) Appl. No.: 11/442,756

(22) Filed: May 30, 2006

(65) Prior Publication Data

US 2008/0097396 A1    Apr. 24, 2008

(51) Int. Cl.
    *B29C 65/00*    (2006.01)
(52) U.S. Cl. .................. 264/261; 264/248; 604/524; 604/525
(58) Field of Classification Search ............ 604/525, 604/531; 264/262, 299, 313, 261
    See application file for complete search history.

(56) References Cited

U.S. PATENT DOCUMENTS

| | | | |
|---|---|---|---|
| 4,782,834 A | 11/1988 | Maguire et al. | |
| 4,917,667 A | 4/1990 | Jackson | |
| 4,976,690 A | 12/1990 | Solar et al. | |
| 5,188,593 A | 2/1993 | Martin | |
| 5,250,069 A | 10/1993 | Nobuyoshi et al. | |
| 5,254,107 A | 10/1993 | Soltesz | |
| 5,279,596 A | 1/1994 | Castaneda et al. | |
| 5,336,205 A | 8/1994 | Zenzen et al. | |
| 5,358,493 A | 10/1994 | Schweich, Jr. et al. | |
| 5,437,288 A * | 8/1995 | Schwartz et al. | ............ 600/585 |
| 5,445,624 A | 8/1995 | Jimenez | |
| 5,470,322 A | 11/1995 | Horzewski et al. | |
| 5,509,910 A | 4/1996 | Lunn | |
| 5,531,719 A | 7/1996 | Takahashi | |
| 5,533,985 A | 7/1996 | Wang | |
| 5,569,218 A | 10/1996 | Berg | |
| 5,622,665 A | 4/1997 | Wang | |
| 5,649,909 A | 7/1997 | Cornelius | |
| 5,658,263 A | 8/1997 | Dang et al. | |
| 5,676,659 A | 10/1997 | McGurk | |
| 5,700,252 A | 12/1997 | Klingenstein | |
| 5,728,063 A | 3/1998 | Preismann et al. | |
| 5,749,849 A | 5/1998 | Engelson | |
| 5,759,173 A | 6/1998 | Preismann et al. | |
| 5,762,637 A | 6/1998 | Berg et al. | |
| 5,772,641 A | 6/1998 | Wilson | |
| 5,775,327 A | 7/1998 | Randolph et al. | |
| 5,836,925 A | 11/1998 | Soltesz | |
| 5,851,203 A | 12/1998 | van Muiden | |
| 5,911,715 A | 6/1999 | Berg et al. | |
| 5,951,929 A | 9/1999 | Wilson | |

(Continued)

FOREIGN PATENT DOCUMENTS

| | | |
|---|---|---|
| WO | WO 97/10022 | 3/1997 |
| WO | WO 97/14466 | 4/1997 |

*Primary Examiner*—Christina Johnson
*Assistant Examiner*—Galen Hauth
(74) *Attorney, Agent, or Firm*—Crompton, Seager & Tufte, LLC

(57) ABSTRACT

Medical devices including a proximal tubular member, a distal tubular member, and an intermediate tubular member connecting the proximal tubular member to the distal tubular member, and related methods.

20 Claims, 7 Drawing Sheets

U.S. PATENT DOCUMENTS

| | | | |
|---|---|---|---|
| 5,980,505 | A | 11/1999 | Wilson |
| 6,021,340 | A | 2/2000 | Randolph et al. |
| 6,030,369 | A | 2/2000 | Engelson et al. |
| 6,036,677 | A | 3/2000 | Javier, Jr. et al. |
| 6,045,547 | A | 4/2000 | Ren et al. |
| 6,059,769 | A | 5/2000 | Lunn et al. |
| 6,093,177 | A | 7/2000 | Javier, Jr. et al. |
| 6,103,037 | A | 8/2000 | Wilson |
| 6,106,510 | A | 8/2000 | Lunn et al. |
| 6,135,992 | A | 10/2000 | Wang |
| 6,139,525 | A | 10/2000 | Davis-Lemessy et al. |
| 6,168,588 | B1 | 1/2001 | Wilson |
| 6,197,015 | B1 | 3/2001 | Wilson |
| 6,355,027 | B1 | 3/2002 | Le et al. |
| 6,503,353 | B1 | 1/2003 | Peterson et al. |
| 6,530,938 | B1 | 3/2003 | Lee et al. |
| 6,648,024 | B2 | 11/2003 | Wang |
| 6,663,614 | B1 | 12/2003 | Carter |
| 6,702,802 | B1 | 3/2004 | Hancock et al. |
| 6,793,634 | B2 | 9/2004 | White et al. |
| 6,974,557 | B1 * | 12/2005 | Webler et al. ............... 264/443 |
| 2002/0077654 | A1 | 6/2002 | Javier, Jr. et al. |
| 2002/0156459 | A1 | 10/2002 | Ye et al. |
| 2002/0156460 | A1 | 10/2002 | Ye et al. |
| 2004/0065979 | A1 | 4/2004 | Wang |
| 2004/0210211 | A1 | 10/2004 | Devens, Jr. et al. |
| 2004/0243102 | A1 | 12/2004 | Berg et al. |

\* cited by examiner

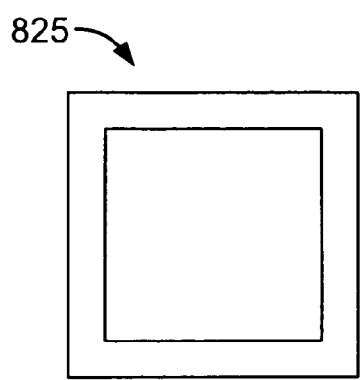
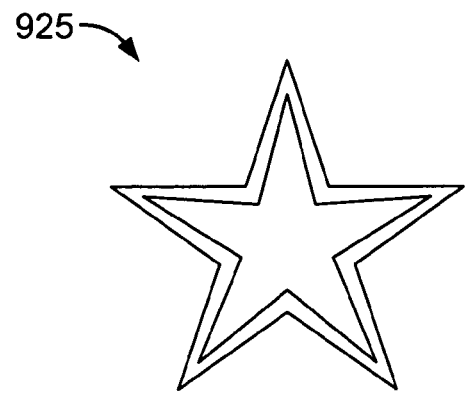
FIG. 11                    FIG. 12
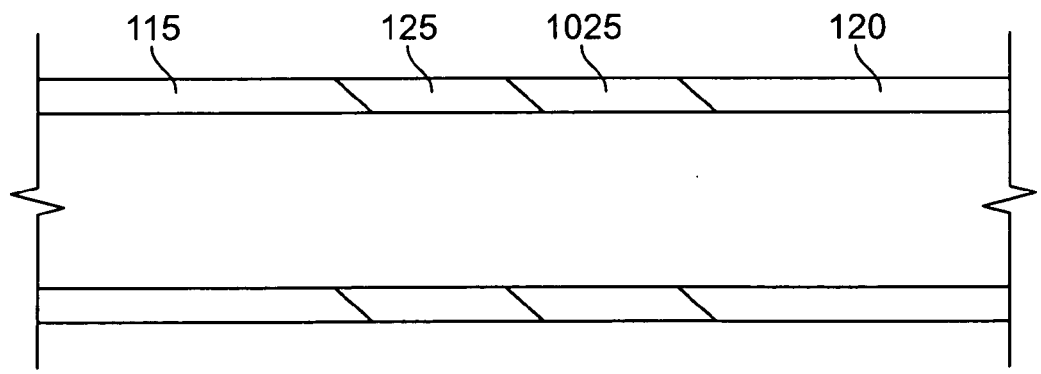
FIG. 13

MEDICAL DEVICES AND RELATED SYSTEMS AND METHODS

TECHNICAL FIELD

The invention relates to medical devices and related systems and methods.

BACKGROUND

Medical devices, such as balloon catheters, are used for a variety of medical procedures. Balloon catheters can be used, for example, to widen an occluded body vessel, as in angioplasty, to position an endoprosthesis, such as a stent or a graft, or to selectively block a passageway. A balloon catheter may include an inflatable and deflatable balloon positioned on a long and narrow catheter body. Initially, the balloon is folded around the catheter body to reduce the radial profile of the balloon catheter for easy insertion into the body.

During an angioplasty procedure, the folded balloon is positioned at a location in a vessel occluded by a stenosis by threading the balloon catheter through a guide catheter and over a guide wire emplaced in the vessel. The balloon is then inflated, e.g., by introducing a fluid into the interior of the balloon. Inflating the balloon can radially expand the stenosis to permit an increased rate of blood flow through the vessel. After use, the balloon is deflated and withdrawn from the body.

SUMMARY

In one aspect of the invention, a method of manufacturing a medical device includes disposing first and second tubular portions in an axially spaced arrangement within a cavity at least partially defined by a mold. Each of the first and second tubular members includes a lumen extending therethrough. Molten resin is delivered into a region of the mold between the first and second tubular members. The resin, when set, forms an intermediate tubular member having a composition that differs from a composition of at least one of the first and second tubular members. A tip is disposed at a distal end region of the medical device.

In another aspect of the invention, a medical device includes a proximal tubular member, a distal tubular member, and an intermediate tubular member bonded to a distal end region of the proximal tubular member and bonded to a proximal end region of the distal tubular member. The intermediate tubular member includes at least one material that is thermally incompatible with at least one material of the proximal and distal tubular members.

Embodiments may include one or more of the following features.

In some embodiments, the tip is secured to at least one of the first and second tubular members.

In some embodiments, the method further includes disposing a mandrel within at least one of the lumens of the first and second tubular members.

In some embodiments, the mold includes at least one recessed region extending outwardly from and in fluid communication with the cavity.

In some embodiments, the at least one recessed region includes a channel extending circumferentially about the cavity.

In some embodiments, the recessed region includes a helical channel.

In some embodiments, the mold includes multiple recessed regions axially spaced along the mold.

In some embodiments, the mold is configured to substantially prevent the first and second tubular members from moving axially relative to one another when the first and second tubular members are disposed within the mold.

In some embodiments, the resin has a melting temperature that is lower than a melting temperature of the first and second tubular members.

In some embodiments, the resin has a melting temperature that is higher than a melting temperature of the first and second tubular members.

In some embodiments, the method further includes heating the mold to a temperature that is lower than a melting temperature of the first and second tubular members.

In some embodiments, the method further includes heating the mold to a temperature that is lower than a melting temperature of the first and second tubular members, and rapidly injecting the resin into the cavity of the mold before the resin cools and solidifies.

In some embodiments, the resin and at least one of the first and second tubular members are thermally incompatible.

In some embodiments, the method further includes disposing the intermediate tubular member in a predetermined region of the medical device. The predetermined region of the medical device is positioned within a predetermined region of a vessel during use of the medical device.

In some embodiments, the predetermined region of the vessel includes a region of the vessel bent at an angle of at least about 70 degrees.

In some embodiments, the predetermined region of the vessel includes a region in which an aorta and a coronary artery are connected.

In some embodiments, the intermediate tubular member has a hardness that is less than a hardness of at least one of the first and second tubular members.

In some embodiments, the intermediate tubular member has a hardness that is greater than a hardness of at least one of the first and second tubular members.

In some embodiments, the predetermined region of the medical device is determined by measuring an axial distance from a distal end region of the medical device.

In some embodiments, the method further includes removing material from at least one end region of each of the first and second tubular members. Each of the end regions include a surface that extends at an acute angle relative to a longitudinal axis of the medical device after removing the material.

In some embodiments, the method further includes chemically bonding the resin to at least one of the first and second tubular members.

In some embodiments, the medical device includes a flexible tip secured to a distal end region of the medical device.

In some embodiments, the flexible tip is secured to the distal tubular member.

In some embodiments, one of the proximal and distal tubular members includes a metal and another of the proximal and distal tubular members comprises a polymeric material.

In some embodiments, the intermediate tubular member includes at least one raised feature extending from an outer surface of the intermediate tubular member.

In some embodiments, the at least one raised feature extends circumferentially around the intermediate tubular member.

In some embodiments, the at least one raised feature extends helically around the intermediate tubular member.

In some embodiments, the intermediate tubular member includes a plurality of raised features axially spaced along the intermediate tubular member.

In some embodiments, the raised features are spaced by increasing distances from a proximal region of the intermediate tubular member to a distal region of the intermediate tubular member.

In some embodiments, the at least one raised feature and the intermediate tubular member are integrally molded with one another.

In some embodiments, the intermediate tubular member decreases in hardness from a proximal region of the intermediate tubular member to a distal region of the intermediate tubular member.

In some embodiments, the intermediate tubular member has a hardness that is less than a hardness of the proximal tubular member and is greater than a hardness of the distal tubular member.

In some embodiments, the intermediate tubular member has a hardness that is less than both a hardness of the proximal tubular member and a hardness of the distal tubular member.

In some embodiments, the intermediate tubular member includes one or more therapeutic agents.

In some embodiments, the intermediate tubular member is chemically bonded to at least one of the proximal and distal tubular members.

In some embodiments, the intermediate tubular member is positioned at a predetermined region of the medical device, and the predetermined region of the medical device is positioned within a predetermined region of a vessel during use of the medical device.

In some embodiments, the intermediate tubular member includes (e.g., is formed of) a fiber composite, a clay composite, a polymer blend, a polymer alloy, a curable polymer, and/or a cross-linkable polymer.

In some embodiments, the intermediate tubular member includes one or more additives (e.g., clays, fibers, etc.).

Embodiments may include one or more of the following advantages.

In some embodiments, the medical devices include proximal and distal tubular members that include incompatible (e.g., thermally incompatible) materials. Embodiments of methods described herein allow such proximal and distal tubular members to be connected to one another via an intermediate tubular member, for example.

In certain embodiments, the intermediate tubular member is disposed at a predetermined location along the medical device. For example, the intermediate tubular member can be a flexible member arranged so that it becomes positioned within a tortuous region of a vessel during use (e.g., during deployment of an endoprosthesis). This design can help to improve the precision with which an endoprosthesis is deployed within the vessel. The medical device can similarly be tailored to function well within vessels of various other shapes and sizes by disposing the intermediate member at a predetermined location along the medical device that is disposed within a particular region of the vessel during use.

In some embodiments, the intermediate tubular member includes one or more raised features extending from a surface (e.g., an outer surface) of the intermediate tubular member. The raised features can help to prevent kinking of the intermediate tubular member during use, help to increase radial strength of the intermediate tubular member, and/or help to provide variable flexibility along the length of the intermediate tubular member. Using the methods described herein, tubular members with raised features can be manufactured inexpensively.

In certain embodiments, the intermediate tubular member is more flexible than the proximal tubular member and is less flexible than the distal tubular member. Thus, the intermediate tubular member can provide a relatively smooth transition in flexibility between the proximal and distal tubular members, for example, as compared to designs in which the proximal and distal tubular members are directly attached to one another (e.g., via a thermal bond). In some embodiments, the intermediate tubular member has a variable flexibility along its length, which can further help to create a smooth transition in flexibility between the proximal and distal tubular members.

In some embodiments, one or more physical properties (e.g., hardness, flexibility) of the intermediate tubular member can be altered by altering the amount of shear applied to the resin. For example, as the amount of shear applied to the resin increases, the resin (e.g., polymer resin) can degrade and become less hard. Thus, the hardness of the intermediate tubular member can be varied along its length by varying the amount of shear applied to the resin delivered to the molding device. As an example, a gradient (e.g., a hardness gradient) can be provided along the length of the intermediate tubular member using a single resin composition.

In certain embodiments, the proximal and distal tubular members (e.g., the distal end region of the proximal tubular member and the proximal end region of the distal tubular member) are pre-treated to provide better adhesion between the intermediate tubular member and the proximal and distal tubular members. In some embodiments, the pre-treatment of the proximal and distal tubular members includes functionalizing surfaces of these tubular members.

Other aspects, features, and advantages of the invention will be apparent from the description and drawings, and from the claims.

DESCRIPTION OF DRAWINGS

FIGS. 9-12 illustrate embodiments of tubular members having various different cross sectional shapes.

FIG. 13 is a cross-sectional view of a catheter shaft including two intermediate components.

DETAILED DESCRIPTION

In general, the medical devices include a proximal tubular member, a distal tubular member, and an intermediate member that connects the proximal and distal tubular members. The proximal and distal tubular members can include (e.g., can be formed of) thermally incompatible materials. Methods of manufacturing the medical devices may include disposing portions of the proximal and distal tubular members in an axially spaced arrangement within a mold, and injecting molten resin into a void within the mold between the proximal and distal tubular members.

Figure 1:
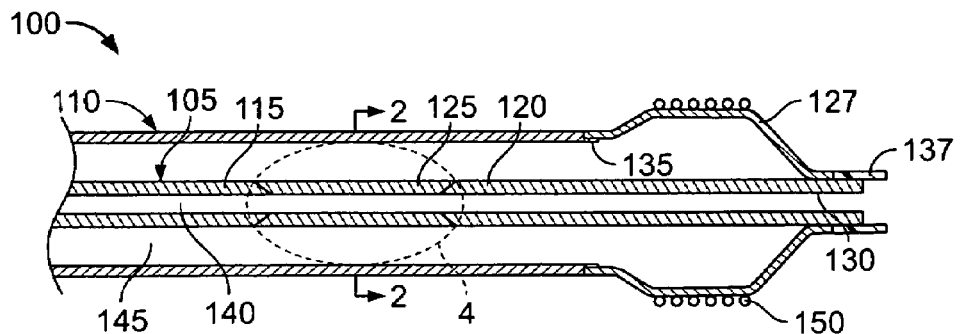
FIG. 1 is a cross sectional view of an embodiment of a balloon catheter.
Figure 2:
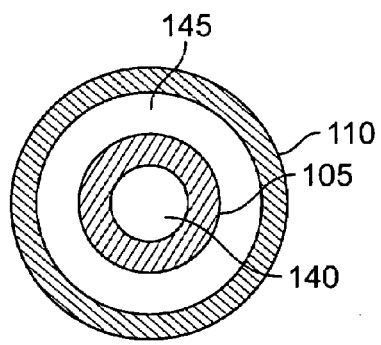
FIG. 2 is a cross sectional view taken along line 2-2 in FIG. 1.

Referring to FIG. 1, a balloon catheter 100 includes an inner catheter shaft 105 and an outer catheter shaft 110. Inner catheter shaft 105 includes a proximal tubular component 115, a distal tubular component 120, and an intermediate tubular component 125, which connects proximal tubular component 115 to distal tubular component 120. A balloon 127 is attached to a distal end region 130 of distal tubular component 120 and to a distal end region 135 of outer catheter shaft 110. A flexible tip 137 is also attached to distal end region 130 of inner catheter shaft 105 adjacent the distal end of balloon 127. As shown in FIG. 2, inner catheter shaft 105 and outer catheter shaft 110, which extends coaxially about inner catheter shaft 105, are generally circular in cross section. A guide wire lumen 140 extends through inner catheter shaft 105, and an annular inflation lumen 145 extends along catheter 100, between inner catheter shaft 105 and outer catheter shaft 110. A stent 150, as shown in FIG. 1, can be crimped onto the outer surface of balloon 127.

In certain embodiments, proximal component 115 (e.g., one or more materials of proximal component 115) is incompatible (e.g., thermally incompatible) with distal component 120 (e.g., one or more materials of distal component 120). One of the proximal and distal components 115 and 120 may degrade before the other of the components reaches its softening point or melting point. The components may have melting points that differ to a degree that makes fabrication (e.g., by thermally bonding the components together) impractical or impossible. For example, proximal component 115 can have a melting temperature that differs from a melting temperature of distal component 120 by at least about 15 degrees Celsius (e.g., at least about 25 degrees Celsius, at least about 50 degrees, at least about 75 degrees Celsius, at least about 100 degrees Celsius, at least about 125 degrees Celsius, at least about 150 degrees Celsius). In certain embodiments, the melting temperature of proximal component 115 differs from the melting temperature of distal component 120 by no more than about 160 degrees Celsius (e.g., no more than about 150 degrees Celsius, no more than about 125 degrees Celsius, no more than about 100 degrees Celsius, no more than about 75 degrees Celsius, no more than about 50 degrees Celsius, no more than about 25 degrees Celsius). The melting temperatures of proximal and distal components 115, 120 can, for example, differ by about 15 degrees Celsius to about 160 degrees Celsius (e.g., about 50 degrees Celsius to about 100 degrees Celsius).

As an alternative to or in addition to being thermally incompatible, the materials of proximal and distal inner components 115 and 120 can be incompatible with one another in other ways. In certain embodiments, for example, the materials are chemically incompatible. As an example, one of proximal and distal components 115, 120 can be formed of a hydrophilic material, such as Nylon 12, while the other of proximal and distal components 115, 120 can be formed of a hydrophobic material, such as low-density polyethylene (LDPE). As an example, one of proximal and distal components 115, 120 can be formed of a material, such as PVC and/or CPVC, that is typically degraded by thermal bonding techniques, while the other of proximal and distal components 115, 120 can be formed of one or more materials that are capable of withstanding thermal bonding techniques. In some embodiments, proximal and/or distal components 115, 120 include a wire braid (e.g., a stainless steel wire braid), which can tend to exacerbate degradation caused by certain heat-related bonding techniques.

Due to the incompatibility of the materials of proximal and distal components 115 and 120, it would be difficult to directly join those components using certain attachment techniques that utilize heat, such as thermal bonding and/or laser bonding. In some embodiments, however, intermediate component 125 includes one or more materials that are compatible with the materials of both proximal component 115 and distal component 120. In such embodiments, intermediate component 125 can be attached to each of the proximal and distal components 115 and 120 regardless of their compatibility with one another, thereby joining proximal and distal components 115 and 120 together along inner catheter shaft 10S.

Figure 4:
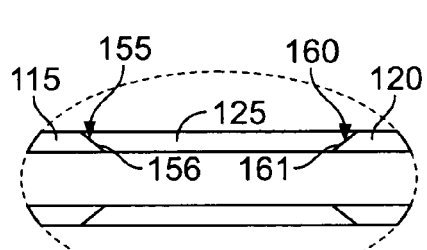
FIG. 4 is an enlarged view of region 4 in FIG. 1.

In certain embodiments, as shown in FIG. 4, a distal end 155 of proximal component 115 and a proximal end 160 of distal component 120 are tapered. As a result, the surface area of bonded regions 156 and 161 between intermediate component 125 and proximal component 115 and between intermediate component 125 and distal component 120 can be increased relative to bond regions between untapered shafts. Increasing the surface area of the bond region can help to increase the bond strength. Thus, the bond between intermediate component 125 and proximal and distal components 115 and 120 can be relatively strong, as compared to the bond created between two untapered tubular members.

In some embodiments, intermediate component 125 is more flexible than proximal component 115 and is less flexible than distal component 120. Thus, intermediate component 125 can help to provide a smooth transition in flexibility between the relatively rigid proximal component 115 and the relatively flexible distal component 120, which can help to prevent kinking and/or buckling of inner shaft 105 during use. In some embodiments, for example, intermediate component 125 has a hardness that is less than the hardness of proximal component 115 and greater than the hardness of distal component 120. Intermediate component 125 can, for example, have a hardness that is about 20 D to about 40 D less than the hardness of proximal component 115 and about 40 A to about 50 A greater than the hardness of distal component 120. Alternatively or additionally, the wall thickness of intermediate component 125 can differ from the wall thickness of proximal component 115 and/or distal component 120. In certain embodiments, for example, the wall of intermediate component 125 is thinner than the wall of proximal component 115 and/or thicker than the wall of distal component 120. For example, the wall of intermediate component 125 can be about 0.07 millimeter to about 0.12 millimeter thinner than the wall of proximal component 115 and/or about 0.07 millimeter to about 0.12 millimeter thicker than distal component 120.

In certain embodiments, intermediate component 125 is chemically bonded to one or both of proximal and distal components 115 and 120. For example, intermediate component 125 can include a curable adhesive (e.g., a UV curable adhesive) that can be chemically bonded to one or both of proximal and distal components 115 and 120 upon being cured (e.g., upon being exposed to ultraviolet energy). Examples of adhesives include epoxies, phenolics, urethanes, anaerobics, acrylics, cyanoacrylates, silicones, polysulfides, and elastomeric adhesives.

Intermediate component 125 and proximal and distal components 115 and 120 can include materials that maintain continuous flexural properties, do not collapse or pinch during use, can be coated with a lubricious material, have good tensile strengths, and/or can be sterilized. In certain embodiments, intermediate component 125 includes a microfibrillar composite, alloy, or blend. Intermediate component 125 can, for example, include one or more polymers, such as polyurethanes, poly-ether-amides, poly butyrates, poly-vinyl butyrates, polyacrilonitriles, acrilonitrile-butyrate-acetate (ABS) tri-polymer, poly acetates, poly vinyl acetates, PVC, CPVC, FEP, PTFE, polyacetals, polyolefins, polyamides (e.g., nylon 12, nylon 11, nylon 6/12, nylon 6, and nylon 66), polyesters, polyethers, polyureas, polyvinyls, polyacrylics, fluoropolymers, and copolymers and block copolymers thereof. Intermediate component 125 can, for example, include block copolymers of polyether and polyamide, such as Pebax® (e.g., Pebax® with a relatively high durometer value, such as 50). In some embodiments, intermediate component 125 includes a clay, silica, or metallic nanocomposite.

In some embodiments, intermediate component 125 includes one or more cross-linking agents. The cross-linking agents can increase the strength, flexibility, and/or extensibility of intermediate component 125. Intermediate component 125 can have a different material composition than proximal and/or inner components 115, 120.

Proximal component 115 and/or distal component 120 can include one or more polymeric materials. Exemplary polymeric materials include thermoplastics and thermosets. Examples of thermoplastics include, for example, polyolefins; polyamides, such as nylon 12, nylon 11, nylon 6/12, nylon 6, and nylon 66; polyesters; polyethers; polyurethanes; polyureas; polyvinyls; polyacrylics; fluoropolymers; copolymers and block copolymers thereof, such as block copolymers of polyether and polyamide, e.g., Pebax® (e.g., Pebax® with a relatively high durometer value, such as 50); and mixtures thereof. Examples of thermosets include elastomers such as EPDM, epichlorohydrin, nitrile butadiene elastomers, silicones, etc. Conventional thermosets such as epoxies, isocyanates, etc., can also be used. Biocompatible thermosets, for example, biodegradable polycaprolactone, poly(dimethylsiloxane) containing polyurethanes and ureas, and polysiloxanes, may also be used. One or more of these materials can be used in any combination.

Other polymeric materials include, for example, elastomers such as thermoplastic elastomers and engineering thermoplastic elastomers, such as polybutylene terephthalate-polyethene glycol block copolymers, which are available, for example, as HYTREL®. Elastomers are discussed, for example, in Hamilton U.S. Pat. No. 5,797,877, which is incorporated herein by reference in its entirety. Other polymers include liquid crystal polymers (LCP's). Examples of LCPs include polyester(s), polyamide(s) and/or their copolymers, such as VECTRA® A (Ticona), VECTRA® B (Ticona) and VECTRA® LKX (Ticona) (e.g., VECTRA® LKX 1111 (Ticona)). Alternatively or additionally, proximal component 115 and/or distal component 120 can include one or more metals, such as steel, aluminum, titanium, platinum, gold, copper, zinc, iron, Bismuth, Barium, and/or one or more salts from these metals.

In some embodiments, proximal component 115 includes (e.g., is formed of) the same type of material or material combination as distal component 120. Alternatively, proximal component 115 can include (e.g., can be formed of) a different type of material or material combination than distal component 120. In certain embodiments, for example, proximal component 115 includes one or more nylons, such as nylon 12, and distal component 120 includes one or more polyether block amides, such as Pebax. In such embodiments, intermediate component 125 can include one or more polyurethanes, which are capable of being bonded (e.g., chemically bonded) to both nylons and polyether block amides.

The dimensions of proximal component 115, distal component 120, and intermediate component 125 can vary depending on the intended use of the balloon catheter. The lengths of the components can, for example, vary. In some embodiments, intermediate component 125 is shorter than proximal component 115 and/or distal component 120. In certain embodiments, intermediate component 125 is longer than proximal component 115 and/or distal component 120. In certain embodiments, intermediate component has a length of about 0.5 centimeter to about 20 centimeters (e.g., about one centimeter to about five centimeters, about five centimeters to about ten centimeters, about ten centimeters to about 20 centimeters).

Figure 5A:
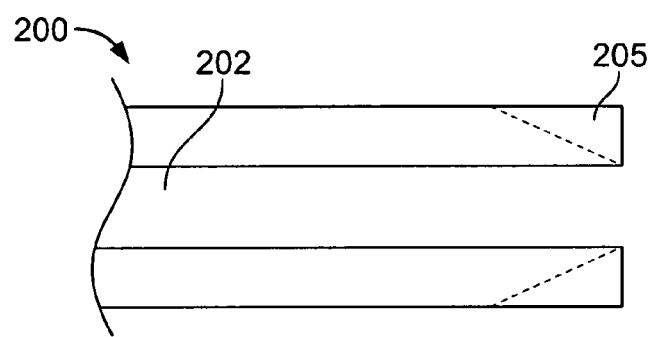
FIGS. 5A-5F illustrate an embodiment of a method of making a catheter shaft of the balloon catheter of FIG. 1.
Figure 5B:
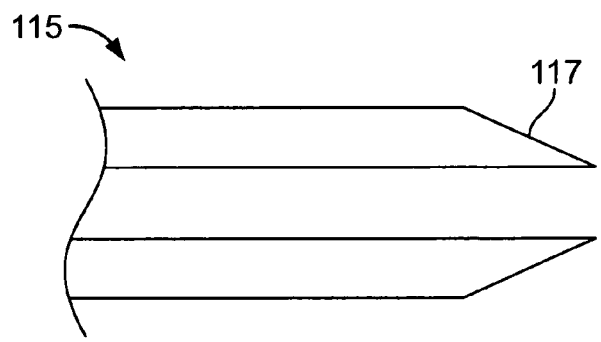

FIGS. 5A-5D illustrate an embodiment of a method of manufacturing inner catheter shaft 105 of balloon catheter 100. As shown in FIG. 5A, the method begins with a tubular member 200. Material is removed from a circumferential end region 205 of tubular member 200 to form proximal inner component 115, as shown in FIG. 5B. The material from end region 205 of tubular member 200 can be removed using one or more material removal techniques, such as centerless grinding, cryogenic grinding, machining, skiving, laser ablation, etc. While removing material from tubular member 200, a support member (e.g., a polytetrafluoroethylene coated steel shaft) can be disposed within a lumen 202 of tubular member 200. The support member can help to stabilize tubular member 200 during the material removal process. In certain embodiments, the support member can rotate tubular member 200 during the material removal process to help ensure that material is evenly removed around the circumference of tubular member 200. As an alternative to or in addition to removing material from tubular member 200, tubular member 200 can be molded into a desired shape (e.g., the desired shape of proximal inner component 115).

Proximal inner component 115, as shown in FIG. 5B, includes a taper 117 at the end from which the material was removed from tubular member 200 (e.g., at the distal end of proximal inner component 115). Taper 117 provides a bond region with an increased surface area. As an alternative to or in addition to taper 117, material can be removed from the end of tubular member 200 to form other shapes that result in an increased surface area to which another tubular member can be bonded. For example, material can be removed in a manner to provide an end region with a double taper (e.g., an end region that both tapers inward from an outer surface and tapers outward from an inner surface). As another example, the end could have a notched shape or beaded shape so as to facilitate a mechanical interlocking of the adjacent components.

A second tubular member (not shown) is also provided, and material is similarly removed from an end region of the second tubular member to form distal inner component 120. The material can be removed from the end region of the second tubular member using one or more of the material removal techniques indicated above.

Figure 5C:
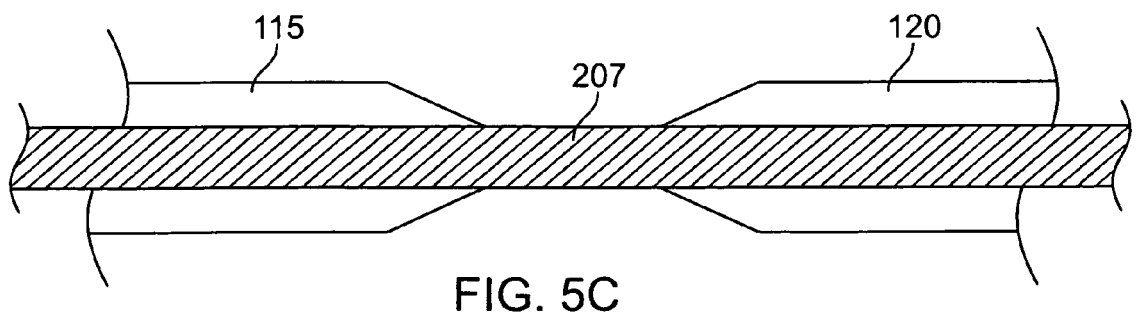

After forming proximal and distal components 115 and 120 from their respective tubular members, proximal and distal components 115 and 120 can be disposed on a mandrel (e.g., a polytetrafluoroethylene coated steel shaft) 207, as shown in FIG. 5C. Proximal and distal components 115 and 120 can be positioned in an axially spaced relationship along mandrel 207. Mandrel 207 can provide structural support to proximal and distal components 115 and 120 during the molding process.

Figure 5D:
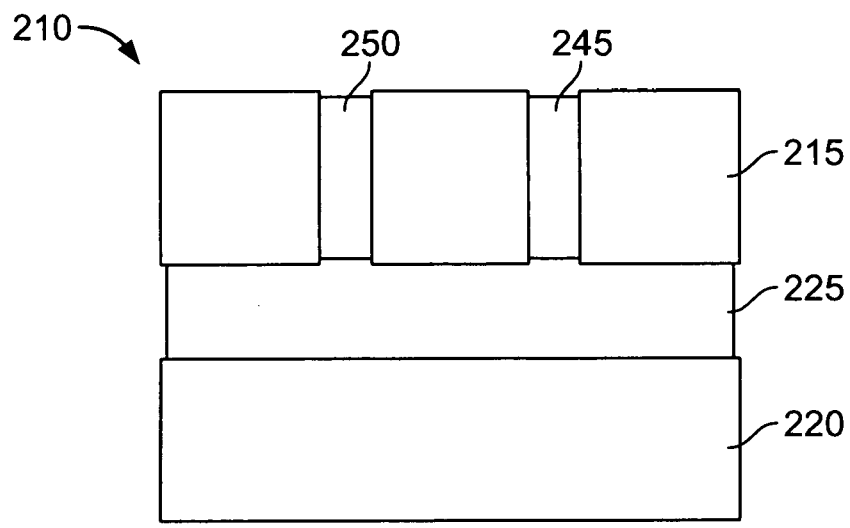

FIG. 5D illustrates a cross sectional view of a molding device 210 that includes a cover 215 and a base 220. When cover 215 is closed, as shown in FIG. 5D, cover 215 and base 220 define a channel 225 therebetween into which mandrel 207 and portions of proximal and distal inner components 115 and 120 can be inserted. Cover 215 includes an inlet passage 245 and an outlet passage 250, both of which are in fluid communication with channel 225. Molding device 210 can include (e.g., can be formed of) one or more materials that have relatively high melting temperatures. For example, molding device 210 can include one or more metals, such as 440 C stainless steel, copper, and/or brass. Alternatively or additionally, molding device can include one or more ceramics and/or one or more glasses, such as silica glass (e.g., Pyrex®) or sapphire glass. In certain embodiments, the inner surface of molding device 210 (e.g., the surface that defines channel 225) is lined with a low friction material, such as PTFE, so that the catheter shaft molded therein can be easily removed from the molding device after being molded.

In some embodiments, molding device 210 is temperature controlled. For example, molding device 210 can include one or more cooling tubes connected to a high temperature cooling device, such as a chiller or a refrigerant. Alternatively or additionally, molding device 210 can include a series of cooling fins, along with appropriately sized forced convection devices (e.g., fans or blowers). In some embodiments, molding device 210 is surrounded by a temperature-controlling jacket, such as an insulated high pressure steam jacket and/or a hot-oil jacket. In certain embodiments, molding device 210 is heated by RF induction heating and cooled by forced convection. Molding device 210 can be heated and/or cooled to help regulate the temperature of the molding device.

Figure 5E:
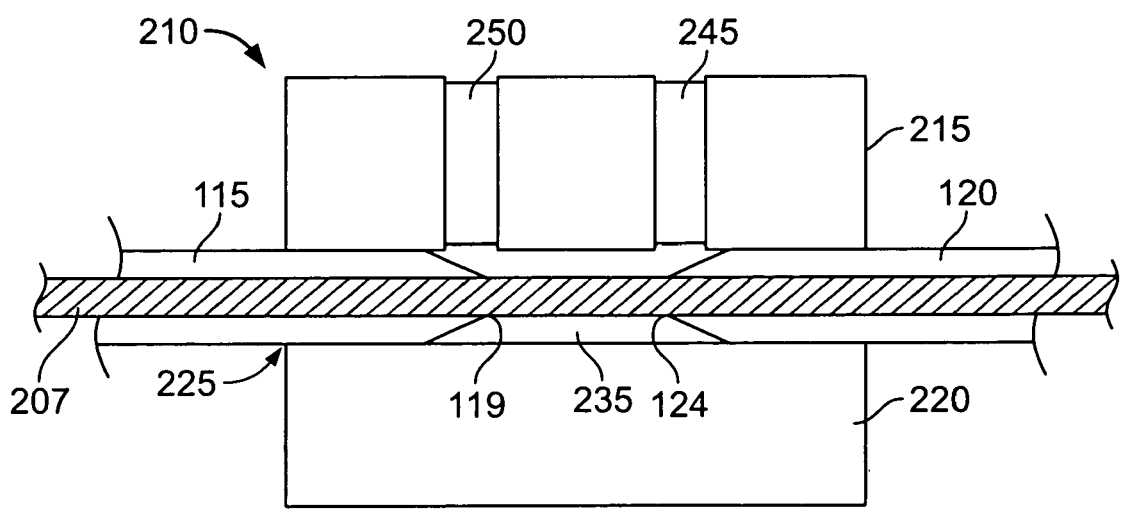

As shown in FIG. 5E, proximal inner component 115 is disposed within a proximal region of channel 225 in molding device 210, and distal inner component 120 is disposed within a distal region of channel 225 in molding device 210. Proximal and distal components 115 and 120 are positioned within molding device 210 in a manner such that a distal end 119 of proximal inner component 115 is axially spaced from a proximal end 122 of distal inner component 120. Proximal and distal components 115 and 120 can, for example, be spaced from one another within molding device 210 by a distance that is substantially equal to the desired length of intermediate component 125. After proximal and distal inner components 115 and 120 are positioned as desired within molding device 210, cover 215 of molding device 210 is closed to secure proximal and distal components 115 and 120 in their respective axial positions. Cover 215 and base 220 of molding device 210 can, for example, compress proximal and distal components 115 and 120 therebetween, when cover 215 is closed, to retain proximal inner component 115 and distal inner component 120 in substantially axially fixed positions relative to one another. Alternatively or additionally, proximal and distal components 115 and 120 can be axially secured by creating a vacuum at outlet passage 250 such that a net inward thrust is created on proximal and distal components 115 and 120.

A tubular void 235 is formed within channel 225, between proximal and distal inner components 115 and 120 and around mandrel 207. As described below, intermediate tubular member 125 can be molded within void 235. Thus, proximal and distal components 115 and 120 can be positioned closer together or farther apart along mandrel 207, depending on the desired length of intermediate component 125. Similarly, the shape of molding device 210 (e.g., the shape of that portion of molding device 210 that defines void 235) can be selected and/or altered based on the desired size and shape of intermediate component 125. In some embodiments, inner surfaces of molding device 210 are lined with a non-stick material, such as PTFE, to facilitate removal of intermediate component 125 from void 235 after being molded therein.

Figure 5F:
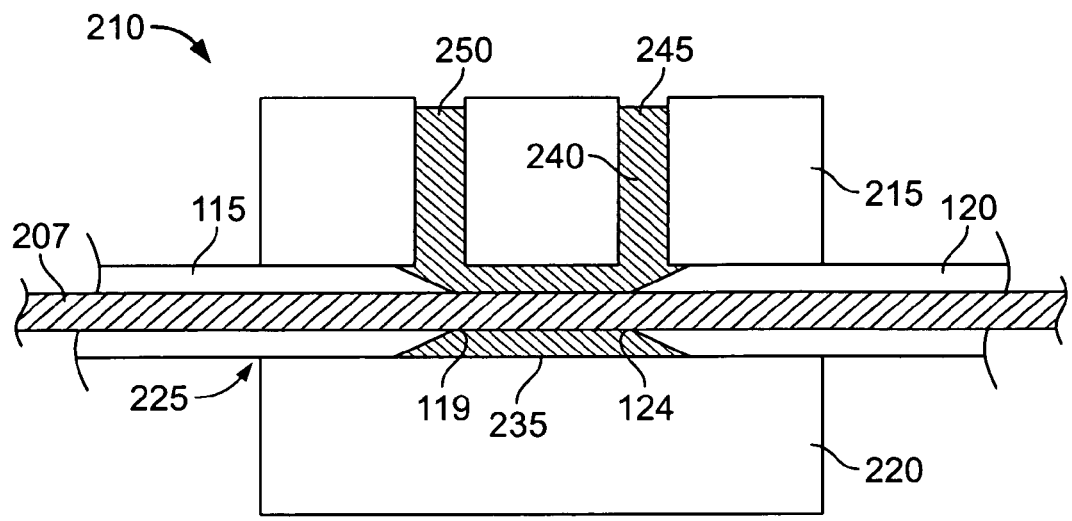

Referring to FIG. 5F, after cover 215 is closed and proximal and distal components 115 and 120 are axially secured, molten resin 240 is injected into tubular void 235 via inlet passage 245. As resin 240 is injected into void 235 via inlet passage 245, air from within void 235 is allowed to escape via outlet passage 250. Alternatively or additionally, air can be evacuated from void 235 via outlet passage 250 (e.g., by applying a vacuum to outlet passage 250) prior to the injection of resin 240. In certain embodiments, inlet passage 245 and/or outlet passage 250 is/are used to introduce inert gases, such as nitrogen and/or argon, into void 235. Resin 240 is injected into void 235 until void 235 has been substantially filled (e.g., until about 98 percent or more by volume of void 235 has been filled with resin). In certain embodiments, void 235 is overfilled (e.g., filled beyond capacity). In such embodiments, excess resin can enter outlet passage 250.

Depending on the composition of resin 240 and the composition of proximal and distal components 115 and 120, resin 240 can be injected at various different temperatures, pressures, and flow rates. In some embodiments, resin 240 is injected into tubular void 235 at a temperature of about 80 degrees Celsius to about 500 degrees Celsius, a pressure of about 300 kPa to about 35,000 kPa and/or a flow rate of about one ml/min to about 1000 ml/min.

Resin 240 can have a viscosity of about 4500 Pa-s or less (e.g., about 3500 Pa-s or less, about 2500 Pa-s or less, about 1500 Pa-s or less, about 1000 Pa-s or less) when injected into void 230. In certain embodiments, resin 240 has a viscosity of about 500 Pa-s to about 4500 Pa-s (e.g., about 1000 Pa-s to about 3500 Pa-s, about 1500 Pa-s to about 2500 Pa-s). Resin 240 can, for example, be heated prior to injection into void 235 until the resin reaches a targeted viscosity. Resin 240 can include one or more of the materials discussed herein with respect to intermediate component 125.

After void 235 has been filled with resin 240, the resin and proximal and distal components 115, 120 are maintained at the mold temperature for a prescribed dwell time. The mold temperature can range from about 130 degrees Celsius to about 230 degrees Celsius. The prescribed dwell time can be of sufficient duration to allow for the completion of the bond between resin 240, proximal component 115 and distal component 120. In some embodiments, the prescribed period of time ranges from about one second to about 30 seconds.

After void 235 has been filled with resin 240 and maintained at the elevated temperature for the prescribed dwell time, the resin is allowed to cool and solidify. In certain embodiments, as discussed above, a cooling device, such as a steam jacket, can be used to control (e.g., increase) the rate at which the resin cools. The cooling time can range from about five seconds to about two minutes. In certain embodiments, as an intermediate step during the cooling process, molding device 210 is maintained at a prescribed temperature (e.g., about 90 degrees Celsius to about 150 degrees Celsius) in order to facilitate annealing of the solidified resin 240. The resin within void 230, when solidified, forms intermediate component 125 of inner shaft 105. Inner shaft 105 can be connected to outer shaft 110 and balloon 127 of balloon catheter 100 using one or more attachment techniques, such as laser bonding and/or adhesive bonding.

Figure 3A:
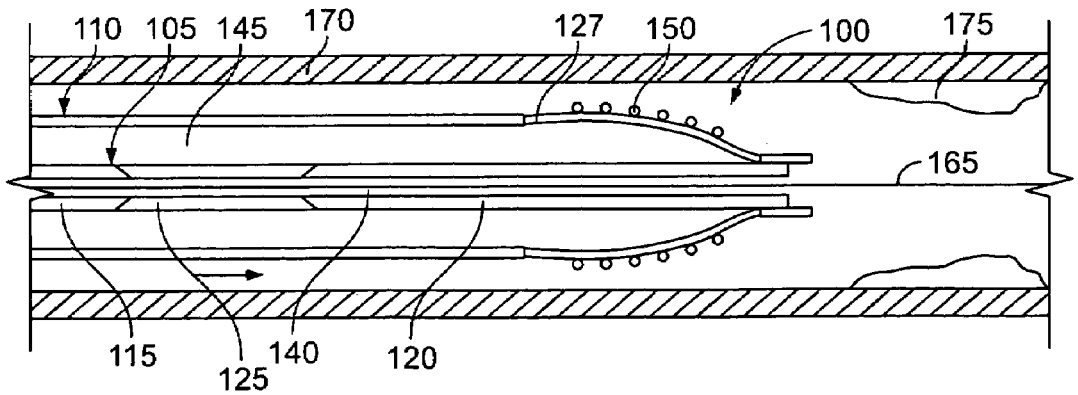
FIGS. 3A-3E illustrate an embodiment of a method of using the balloon catheter of FIG. 1.
Figure 3B:
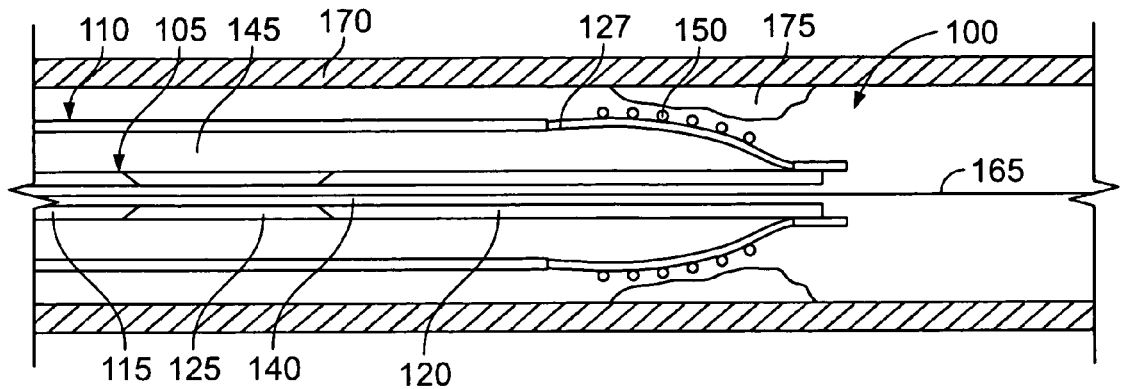
Figure 3C:
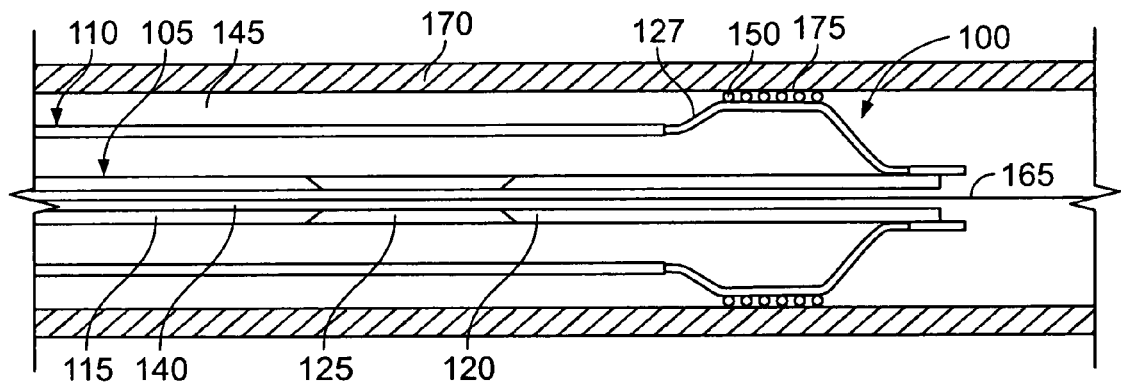
Figure 3D:
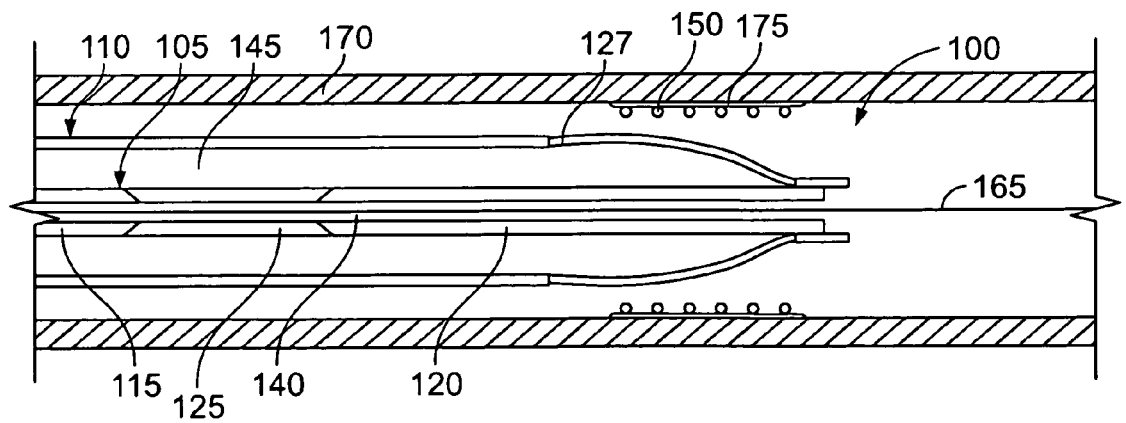
Figure 3E:
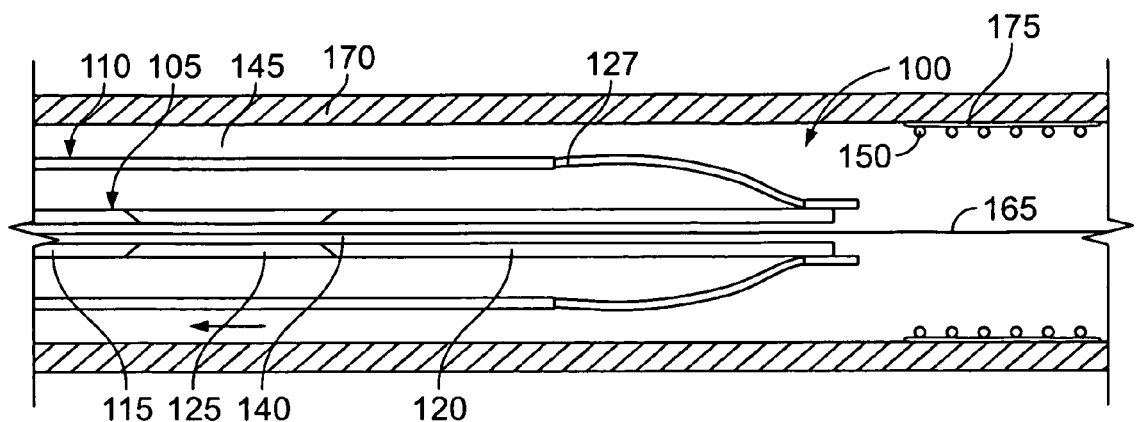

FIGS. 3A-3E show a method of using balloon catheter 100. Referring to FIG. 3A, the method includes inserting a guide wire 165 into a body vessel 170 (e.g., a blood vessel) and then feeding balloon catheter 100 over guide wire 165 so that guide wire 165 is disposed within guide wire lumen 140 of inner catheter shaft 105. Balloon catheter 100 is then advanced along guide wire 165 and through body vessel 170 until the deflated balloon 127 and stent 150 are positioned within an occluded region 175 of vessel 170, as shown in FIG. 3B. After being positioned within occluded region 175 of vessel 170, balloon 127 is inflated to deploy stent 150 within vessel 170, as shown in FIG. 3C. Balloon 127 can be expanded by passing an inflation fluid, such as saline, through annular inflation lumen 145. An inflation mechanism, such as a syringe, can, for example, be connected to a proximal end (not shown) of balloon catheter 100 in order to deliver the inflation fluid to balloon 127. The inflation of balloon 127 and deployment of stent 150 can help to radially expand occlusion 175 and/or to provide radial support in that region of vessel 170. Once stent 150 has been deployed, balloon 127 is deflated and balloon catheter 100 is withdrawn from vessel 170, as shown in FIGS. 3D and 3E.

While various embodiments have been described, other embodiments are possible.

As an example, in some embodiments, the flexibilility of intermediate component 125 varies along its length. For example, intermediate component 125 can become increasingly flexible from its proximal end to its distal end to enhance trackability of the catheter. Intermediate component 125 can, for example, be formed to be increasingly flexible along its length by altering the composition of resin 140 delivered through inlet passage 145. Alternatively or additionally, the wall of intermediate component 125 can become increasingly thinner from a proximal end of the intermediate component to a distal end of the intermediate component. The increasingly thin wall can, for example, be formed by altering the configuration of void 235 and/or mandrel 207.

As another example, in certain embodiments, intermediate component 125 is more flexible than proximal and distal components 115 and 120. Intermediate 125 can be positioned at a region of the catheter that experiences a high degree of flexure during use.

For example, intermediate component 125 can be located at a region of the catheter that is positioned within a tortuous region of the vessel (e.g., at the junction between the aortic artery and the coronary artery) during use. The relatively high degree of flexibility of intermediate component 125 can, for example, help to improve the ability of the catheter to be positioned within and/or pass through the tortuous region of the vessel.

Intermediate component 125 can include one or more materials (e.g., can be formed of one or more materials) that have greater flexibility than the materials of proximal and distal inner components 115 and 120. In certain embodiments, intermediate component 125 includes one or more materials that are softer than the materials of proximal and distal inner components 115 and 120. Intermediate component 125 can, for example, have a hardness that is about 10 D to about 40 D less than a hardness of proximal and distal inner components 115 and 120. Intermediate component 125 can, for example, have a hardness of about 30 D to about 55 D. Alternatively or additionally, intermediate component 125 can be formed to have a thinner wall than proximal component 115 and/or distal component 120.

As an additional example, in some embodiments, one or more therapeutic agent(s) are carried by (e.g., carried within) intermediate component 125. Certain therapeutic agents can, for example, reduce spasmatic responses during balloon angioplasty. The therapeutic agent(s) can be carried by intermediate component 125 using one or more techniques, such as pre-blending the therapeutic agent(s) with the resin of intermediate component 125 and/or coating intermediate component 125 with the therapeutic agent(s). Examples of therapeutic agents include paclitaxel, oxybutynin, belladonna alkaloids, phenobarbital, non-steroidal anti-inflammatory drugs, and heparin.

As a further example, in some embodiments, materials are embedded within intermediate component 125 during the molding process. Electrical conductors (e.g., braided or coiled electrically conductive wires) can, for example, be embedded within the intermediate component. During the molding process shown in FIGS. 5E and 5F, for example, the electrical conductors can be disposed within tubular void 235 such that at least a portion of the electrical conductors become entrapped within resin 240 when resin 240 is injected into molding device 210. As another example, reinforcement elements, such as fiber glass strands, metal fibers, and/or ceramic fibers, can similarly be embedded within intermediate component 125 by disposing the reinforcement elements within tubular void 235 prior to injecting resin 240 into the void. The electrical conductors and reinforcement elements can help to provide intermediate component 125 with increased strength (e.g., increased radial strength).

As another example, the intermediate component can be located at a position along balloon catheter that is predetermined to be positioned within a tortuous region of a blood vessel during use (e.g., during deployment of the stent). The tortuous region of the blood vessel can, for example, have one or more regions that are bent at an angle of at least about 70 degrees (e.g., at least about 90 degrees, about 70 degrees to about 1110 degrees). This positioning of the intermediate component along the catheter can be advantageous, for example, when the intermediate component has a property (e.g., a level of flexibility) that allows it to be more easily positioned within the tortuous region of the vessel than the proximal component and/or distal component. To determine the position along the balloon catheter at which to locate the intermediate component, the region of the vessel in which the balloon catheter is to be used can first be imaged using a technique, such as x-ray, fluoroscopy, or magnetic resonance imaging. Based on the images of the vessel the desired distance between the region of the vessel to be treated (e.g., the occluded region) and the region of the vessel at which to position the intermediate component (e.g., the tortuous region) can be determined. The balloon catheter can then be formed so that the intermediate component is spaced apart from the balloon by a distance that is substantially equal to the distance between the region of the vessel to be treated and the tortuous region of the vessel.

Figure 6:
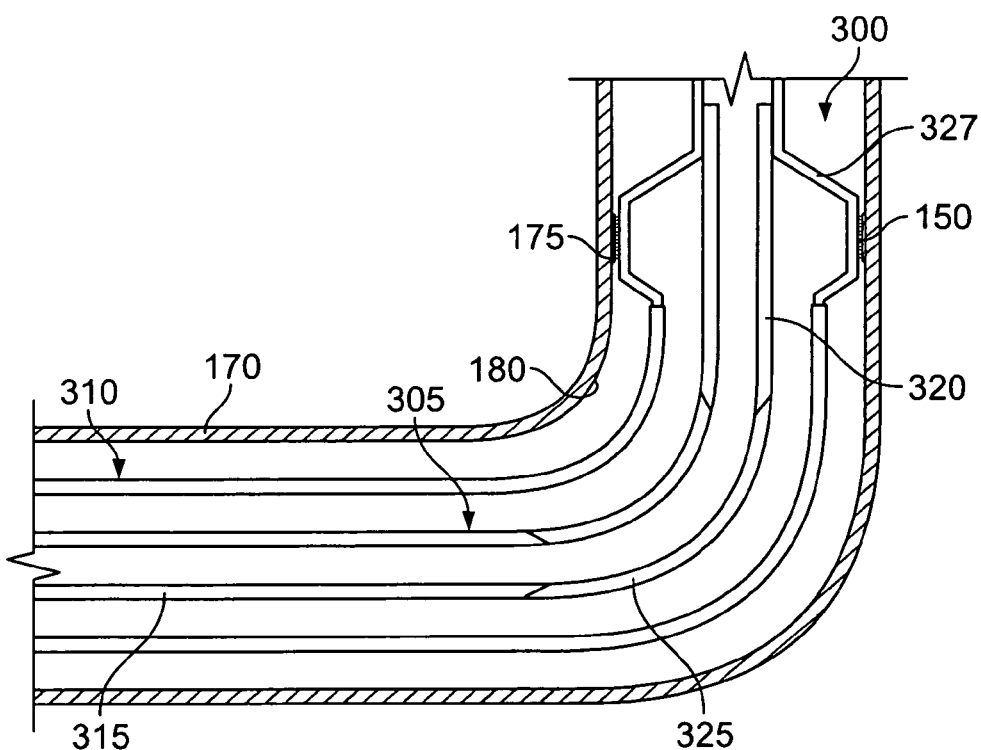
FIG. 6 illustrates an embodiment of a balloon catheter during use.

FIG. 6 illustrates the use of a balloon catheter 300 including an inner catheter shaft 305 and an outer catheter shaft 310. Inner catheter shaft 305 includes an intermediate component 325 that is located in a predetermined position along the balloon catheter to fit within a tortuous or bent region 180 of vessel 170 during use. For example, intermediate component 325 can be arranged to be positioned at a junction between the aorta and coronary artery of a patient during use. Intermediate component 325 is bonded axially between less flexible proximal and distal components 315 and 320. When balloon 327 and stent 150 are positioned as desired, e.g., within occluded region 175 of vessel 170, intermediate component 325 is adjacent tortuous or bent region 180 of vessel 170 (e.g., a region in which the aorta connects to the coronary artery). Because of the increased flexibility of intermediate component 325 relative to proximal and distal components 315 and 320, intermediate component 325 conforms to the bend of the vessel relatively well. Thus, this arrangement can help to improve mobility of the catheter through tortuous vessels. In some embodiments, the arrangement can help to position balloon 327 and stent 150 with improved precision. For example, balloon 327 and stent 150, notwithstanding bend 180, can remain positioned in a generally central location of vessel 170 during use. This positioning can help to increase the precision with which stent 150 is deployed in the vessel.

Figure 7:
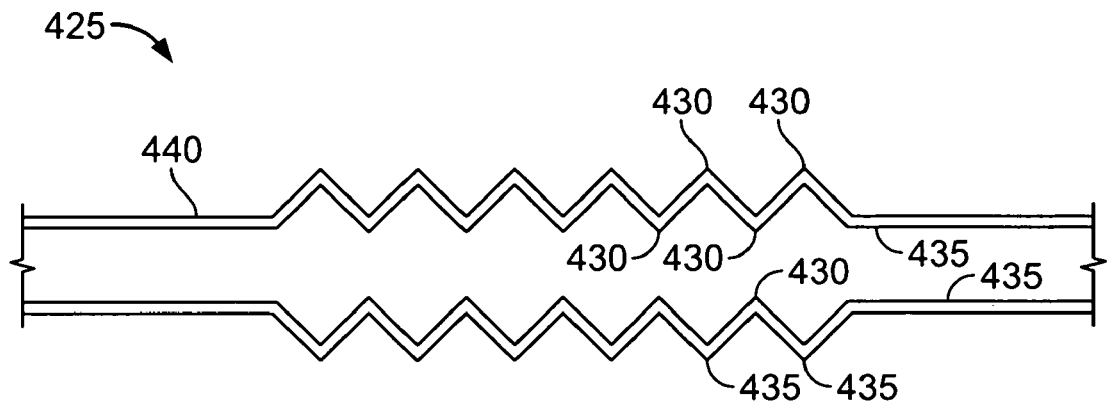
FIGS. 7 and 8 are cross sectional views of embodiments of tubular members including raised features.

As a further example, while the intermediate components of the embodiments above include outer surfaces that are substantially uniform along their lengths, in certain embodiments, the intermediate components can include raised features extending from their surfaces. As shown in FIG. 7, for example, intermediate component 425 is corrugated. In this embodiment, intermediate component 425 includes raised features 430 that extend inwardly from an inner surface 435 and outwardly from an outer surface 440. The corrugated arrangement of intermediate component 425 can help to prevent intermediate component 125 from kinking during use.

The corrugated intermediate component 425 can be molded using methods similar to those described above. The molding device in which intermediate component 425 can include a corrugated inner surface that corresponds to the desired corrugated surface of intermediate component 425. The molding device can, for example, include a central channel and multiple recessed regions that extend outwardly from and are in fluid communication with the central channel. The tubular body of intermediate component 425 can be formed within the channel of the mold and the raised features can be formed within the recessed regions extending outwardly from the channel.

Figure 8:
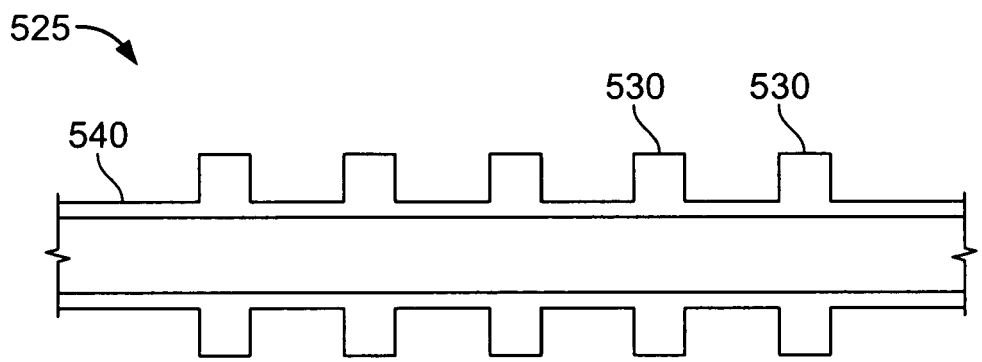

Referring to FIG. 8, as another example, an intermediate component 525 includes annular rings 530 that extend circumferentially about an outer surface 540 of intermediate component 525. In certain embodiments, as shown in FIG. 8, annular rings 530 are substantially evenly spaced along intermediate component 525 and can help to increase the strength of intermediate component 525. In certain embodiments, annular rings 530 can be variably spaced along intermediate component 525. For example, annular rings 525 can become increasingly spaced apart from a proximal end 545 of intermediate component 525 to a distal end 550 of intermediate component 525. As a result, intermediate component 525 can decrease in stiffness from proximal end 545 to distal end 550. As an alternative to or in addition to annular rings, the intermediate component can include a raised helical member that extends along the outer surface of the component.

Intermediate component 525 can be molded in a molding device like those described above. The molding device can, for example, include a central channel and multiple recessed regions that extend outwardly from and are in fluid communication with the central channel. The tubular body of intermediate component 525 can be formed within the channel of the mold and the raised feature(s) can be formed within the recessed regions extending outwardly from the channel.

Figure 9:
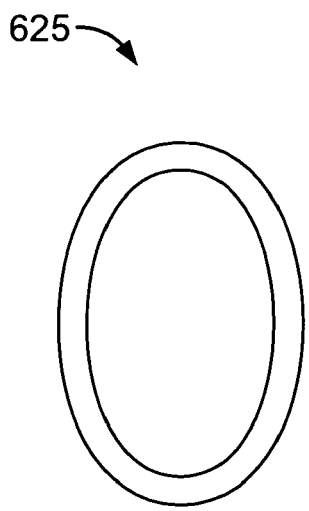
Figure 10:
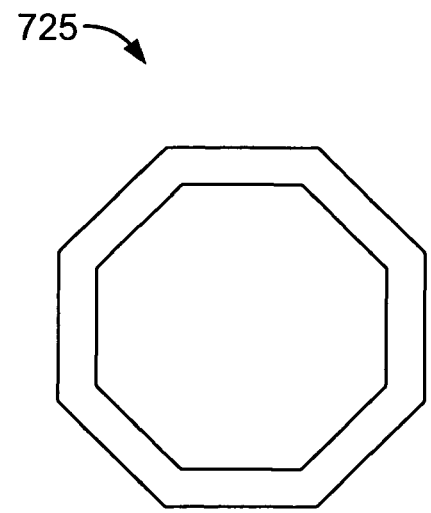

As an additional example, while the embodiments above describe intermediate components with substantially circular cross sections, the intermediate components can alternatively or additionally have other cross sectional shapes. As shown in FIG. 9, for example, an intermediate component 625 has a substantially oval cross sectional shape. Referring to FIG. 10, intermediate 725 has an octagonal cross sectional shape. Intermediate component 825, as shown in FIG. 11, has a square cross sectional shape. As shown in FIG. 12, intermediate component 12 has a generally star-shaped cross section. Intermediate components of non-circular cross sectional shape can be molded by using a molding device that includes a non-circular molding channel or void and/or a mandrel having a non-circular cross sectional shape. In some embodiments, intermediate components with non-circular cross sectional shapes can help to reduce the amount of friction caused by the outer tubular member of the catheter sliding against the inner tubular member of the catheter.

As another example, while embodiments above describe particular materials with which proximal component 115, distal component 120, and intermediate component 125 can be formed, these components can be formed using any of the materials discussed herein in various different combinations. For example, one or more of the materials described herein with respect to proximal and distal components 115, 120 can be used to form intermediate component 125, and vice versa.

As an additional example, while embodiments above describe devices that include a single intermediate component between the proximal and distal components, in some embodiments, devices include multiple (e.g., two or more, three or more, four or more, five or more) intermediate components disposed between proximal and distal components. Referring to FIG. 13, for example, a catheter shaft includes first and second intermediate components 125, 1025 positioned between proximal and distal components 115, 120. In certain embodiments, intermediate components 125 and 1025 have material compositions that differ from one another. In some embodiments, intermediate component 125 is more compatible (e.g., thermally and/or chemically compatible) with proximal component 115 than intermediate 1025, and intermediate component 1025 is more compatible with distal component 120 than intermediate component 125. Thus, by using both intermediate components, rather than only one intermediate component, the bonds between the various components of the catheter shaft can be increased. The catheter shaft can be formed using one or more techniques similar to those described above with respect to balloon catheter 100. Intermediate components 125 and 1025 can, for example, be formed by injecting two different streams of resin into a molding device.

As a further example, while the embodiments described above relate to inner catheter shafts of balloon catheters, other components of balloon catheters can alternatively or additionally include integrally molded proximal, distal, and intermediate components, similar to those described above with respect to inner shafts. In some embodiments, for example, the outer shaft includes integrally molded proximal, distal, and intermediate components. In certain embodiments, both the inner shaft and the outer shaft include such arrangements. In some embodiments, the intermediate component of the outer shaft is axially positioned along the balloon catheter in substantially the same region as the intermediate component of the inner shaft. In certain embodiments, the intermediate component of the outer shaft is arranged along a region of the outer shaft that is predetermined to be positioned adjacent a tortuous region of a vessel during use. Alternatively or additionally, the intermediate component of the outer shaft can be positioned at other locations along outer shaft.

As an additional example, while the embodiments described above relate to balloon catheters, other types of medical devices can similarly include one or more tubular members or shafts like those described herein. Examples of other types of medical devices include self-expanding stent delivery systems (e.g., inner members of self-expanding stent delivery systems, outer sheaths of self-expanding stent delivery systems), guide catheters, endoscopes, cardiac rhythm management (CRM) conductive wires, urologic drainage devices, post-surgical wound drainage devices, and stomach feeding tubes.

The following example illustrates a process for manufacturing a catheter shaft:

Example 1

To form a catheter shaft, a proximal tubular segment constructed from Nylon 12, and a distal tubular segment constructed from Pebax 7033 are provided. The proximal tubular segment has an outer diameter of approximately 0.045 inch (approximately 1.14 millimeters) and an inner diameter of approximately 0.038 inch (approximately 0.965 millimeter).

The distal tubular segment has an outer diameter of approximately 0.028 inch (approximately 0.711 millimeter) and an inner diameter of approximately 0.024 inch (approximately 0.610 millimeter).

A known skiving operation is used to form a taper on a proximal end region of the distal tubular segment and on a distal end region of the proximal tubular segment. For each segment, approximately one centimeter of the shaft is skived. After the skiving operation, the end regions of the tubular segments are trimmed, resulting in a tapered region having a length of one centimeter.

After forming the tapered regions on the proximal and distal tubular segments, a PTFE-coated steel mandrel is inserted through the central lumens of the proximal and distal tubular segments. The coated mandrel is tapered to accommodate the smaller inner diameter of the distal segment and the larger inner diameter of the proximal segment.

The mandrel includes markings made with a dye to assist the technician in correctly positioning each of the segments on the mandrel. The PTFE-coated steel mandrel is arranged to extend distally beyond the distal segment when the proximal and distal segments are appropriately positioned on the mandrel. This arrangement helps to facilitate extraction of the mandrel after completion of the molding procedure discussed below.

After positioning the proximal and distal tubular segments on the mandrel, the assembly of the proximal segment, the distal segment, and the mandrel are placed onto a lower half of an open mold. The mold, when closed, forms a cavity. There is one injector gate at the top of the mold and there are two exit gates at the bottom of the mold. One of the exit gates is at the distal end of the mold and the other is at the proximal end of the mold. The interior portion of the mold is coated with a non-stick surface such as PTFE. The material from which the mold is formed allows for the transmission of ultraviolet light therethrough.

Once the assembly of the distal segment, the proximal segment, and the mandrel is placed onto the lower half of the open mold, the mold is closed and a clamping force of approximately 500 pounds is evenly applied to the mold. The inner diameter of the closed mold, which defines the cavity, is approximately 0.0015 inch (approximately 0.038 millimeter) smaller than the outer diameter of the proximal and distal tubular segments. Thus, the proximal and distal tubular segments are immobilized by the closed mold. Subsequently, the mold is heated to 110° C., and a vacuum of approximately 50 millimeters of mercury is applied to the exit gates so that all of the air is evacuated from the cavity formed by the closed mold. A UV-cured epoxy (e.g., Masterbond UV15-7SP4DC) is then injected into the cavity of the mold at a temperature of 110° C. The duration of the injection is approximately three seconds. After injecting the UV-cured epoxy into the mold, the mold is irradiated with ultraviolet light for one minute to initiate the curing process. The temperature of the mold is then increased to 120° C. for five minutes to allow the epoxy to set, thereby forming the intermediate segment of the catheter shaft. The assembly is then removed from the mold and placed in a chamber for controlled curing of the intermediate segment.

The outer surface of the intermediate segment includes a shallow corrugation. The inner diameter of the intermediate segment is tapered linearly from 0.038 inch (0.965 millimeter) to 0.024 inch (0.610 millimeter). The length of the intermediate segment is approximately eight centimeters long.

Other embodiments are within the scope of the following claims.

What is claimed is:

1. A method of manufacturing a medical device, the method comprising:
   providing a first tubular member, the first tubular member defining a lumen therethrough;
   providing a second tubular member, the second tubular portion defining a lumen therethrough, said second tubular portion provided separately and independently from said first tubular portion;
   disposing the first and the second tubular members in an axially spaced arrangement within a cavity at least partially defined by a mold;
   subsequent to the step of disposing the first and the second tubular members delivering molten resin into a region of the mold between the first and second tubular members, the resin, when set, forming an intermediate tubular member having a composition that differs from a composition of at least one of the first and second tubular members; and
   disposing a tip at a distal end region of the medical device, wherein said tip is not said first tubular portion and is not said second tubular portion,
   wherein the first tubular member has a first polymeric material composition and wherein the second tubular member has a second polymeric material composition different from the first material composition.

2. The method of claim 1, wherein the tip is secured to at least one of the first and second tubular members.

3. The method of claim 1, further comprising disposing a mandrel within at least one of the lumens of the first and second tubular members.

4. The method of claim 1, wherein the mold defines at least one recessed region extending outwardly from and in fluid communication with the cavity.

5. The method of claim 4, wherein the at least one recessed region comprises a channel extending circumferentially about the cavity.

6. The method of claim 4, wherein the recessed region comprises a helical channel.

7. The method of claim 4, wherein the mold defines a plurality of recessed regions axially spaced along the mold.

8. The method of claim 1, wherein the mold is configured to substantially prevent the first and second tubular members from moving axially relative to one another when the first and second tubular members are disposed within the mold.

9. The method of claim 1, wherein the resin has a melting temperature that is lower than a melting temperature of the first and second tubular members.

10. The method of claim 1, further comprising heating the mold to a temperature that is lower than a melting temperature of the first and second tubular members.

11. The method of claim 1, wherein the resin and at least one of the first and second tubular members are thermally incompatible.

12. The method of claim 1, wherein the intermediate tubular member has a hardness that is less than a hardness of at least one of the first and second tubular members.

13. The method of claim 1, further comprising removing material from at least one end region of each of the first and second tubular members, each of the end regions comprising a surface that extends at an acute angle relative to a longitudinal axis of the medical device after removing the material.

14. The method of claim 1, further comprising chemically bonding the resin to at least one of the first and second tubular members.

15. The method of claim 1, wherein the first and second tubular members are thermally incompatible such that direct thermal bonding between the first and second tubular members is impossible or impracticable.

16. The method of claim 13 wherein the step of removing material from at least one end region of each of the first and second tubular member comprises the step of: removing material from an end region of one of the first and second tubular member and separately removing material from an end region of the other of the first and second tubular members.

17. The method of claim 1 wherein the first tubular member has an outer diameter, the second tubular member has an outer diameter, and the mold cavity has an inner diameter, wherein the mold cavity inner diameter is smaller than the outer diameters of the first and second tubular members such that the first and second tubular members are immobilized within the mold when the mold is closed.

18. The method of claim 1 further comprising the steps of:
prior to the step of delivering molten resin, heating the mold;
subsequent to the step of delivering molten resin, raising the temperature of the mold.

19. The method of claim 18 wherein the step of raising the temperature of the mold comprises the step of raising the temperature of the mold to 120 degrees Celsius.

20. A method of manufacturing a medical device, the method comprising:
providing a first tubular member, the first tubular member defining a lumen therethrough;
providing a second tubular member, the second tubular portion defining a lumen therethrough, said second tubular portion provided separately and independently from said first tubular portion;
disposing the first and the second tubular members in an axially spaced arrangement within a cavity at least partially defined by a mold;
subsequent to the step of disposing the first and the second tubular members, delivering molten resin into a region of the mold between the first and second tubular members, the resin, when set, forming an intermediate tubular member having a composition that differs from a composition of at least one of the first and second tubular members; and
disposing a tip at a distal end region of the medical device, wherein said tip is not said first tubular portion and is not said second tubular portion,
wherein the first and second tubular members are thermally incompatible such that direct thermal bonding between the first and second tubular members is impossible or impracticable.

* * * * *